US009801701B2

(12) United States Patent
Schnitzspan et al.

(10) Patent No.: US 9,801,701 B2
(45) Date of Patent: Oct. 31, 2017

(54) METHODS, APPARATUSES, COMPUTER PROGRAMS, AND SYSTEMS FOR CREATING A CUSTOM DENTAL PROSTHESIS USING A CAD/CAM SYSTEM

(71) Applicant: Sirona Dental Systems GmbH, Bensheim (DE)

(72) Inventors: Paul Schnitzspan, Frankfurt (DE); Thorsten Jordan, Pfungstadt (DE)

(73) Assignee: SIRONA DENTAL SYSTEMS GMBH, Bensheim (DE)

( * ) Notice: Subject to any disclaimer, the term of this patent is extended or adjusted under 35 U.S.C. 154(b) by 173 days.

(21) Appl. No.: 14/701,968

(22) Filed: May 1, 2015

(65) Prior Publication Data

US 2016/0317261 A1 Nov. 3, 2016

(51) Int. Cl.
*A61C 13/10* (2006.01)
*A61C 13/08* (2006.01)
*A61C 13/00* (2006.01)
*A61C 13/01* (2006.01)
*A61C 8/00* (2006.01)
*A61C 13/34* (2006.01)

(52) U.S. Cl.
CPC ........ *A61C 13/1003* (2013.01); *A61C 8/0048* (2013.01); *A61C 13/0004* (2013.01); *A61C 13/01* (2013.01); *A61C 13/082* (2013.01); *A61C 13/34* (2013.01); *A61C 8/0095* (2013.01)

(58) Field of Classification Search
CPC ................ A61C 13/01; A61C 13/10
See application file for complete search history.

(56) References Cited

U.S. PATENT DOCUMENTS

| | | | | |
|---|---|---|---|---|
| 4,583,949 A | * | 4/1986 | Heartness | A61C 13/25 433/185 |
| 4,654,006 A | * | 3/1987 | Kusano | A61C 13/04 264/17 |
| 4,957,438 A | * | 9/1990 | Bax | A61C 13/2656 433/177 |
| 5,030,094 A | * | 7/1991 | Nardi | A61C 13/30 433/169 |
| 5,417,570 A | * | 5/1995 | Zuest | A61C 13/2656 433/172 |
| 9,078,720 B2 | * | 7/2015 | Boku | A61C 8/0001 |
| 2002/0039718 A1 | * | 4/2002 | Kwan | A61C 8/0001 433/173 |
| 2002/0090525 A1 | * | 7/2002 | Rusin | A61C 13/0022 428/542.8 |
| 2006/0040235 A1 | * | 2/2006 | Davis | A61C 13/24 433/185 |

* cited by examiner

*Primary Examiner* — Kennedy Schaetzle
(74) *Attorney, Agent, or Firm* — Fitzpatrick, Cella, Harper & Scinto

(57) ABSTRACT

Digital design and/or fabrication of a dental prosthesis that includes a gingiva part having retention pockets and corresponding injection channels that extend from the retention pockets to an exterior of the gingiva part. The positioning of a matrix mated to a ball attachment of a dental implant is fixed in the retention pocket by injection of a curable adhesive through the injection channels and into the retention pockets. The location of the retention pockets and the injection channels may be automatically generated by a computer-aided design/computer-assisted manufacturing (CAD/CAM) system. The gingiva part including the retention pockets and injection channels can further be designed and fabricated by the CAD/CAM system.

17 Claims, 10 Drawing Sheets

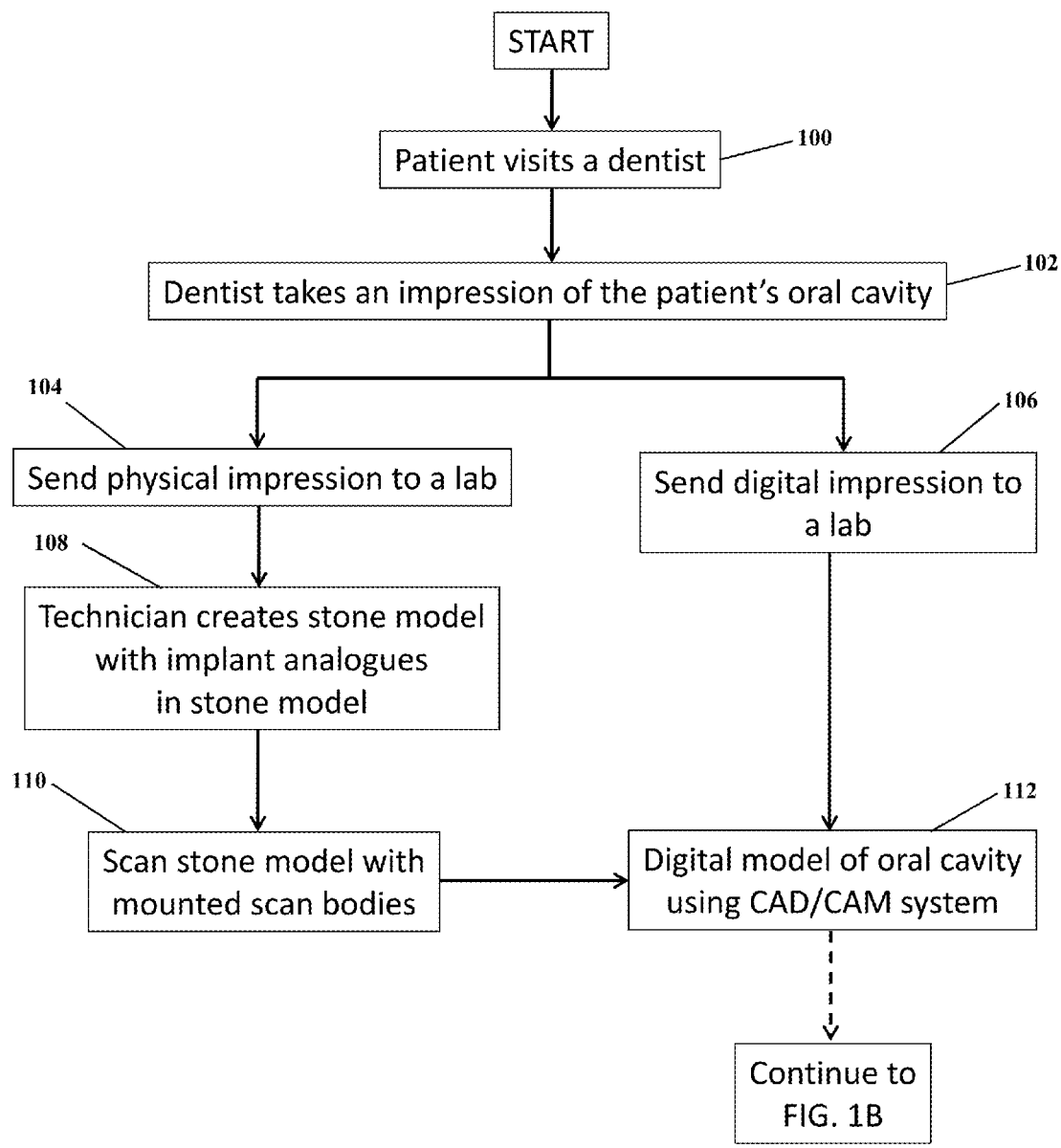

METHODS, APPARATUSES, COMPUTER PROGRAMS, AND SYSTEMS FOR CREATING A CUSTOM DENTAL PROSTHESIS USING A CAD/CAM SYSTEM

BACKGROUND

Field

The present disclosure relates generally to dental restorations, and, in particular, to the use of a CAD/CAM system to produce a dental prosthesis.

Background

Restoring or repairing one or more of a patient's teeth often involves the preparation and attachment of a dental prosthesis such as a crown, bridge, or denture. Dentures are constructed to replace missing teeth and are supported by the surrounding soft and hard tissues of the oral cavity. One type of denture, known as a non-splinted overdenture, comprises a partial or full dental prosthesis that is supported by a ball attachment on a dental implant. The non-splinted overdenture generally includes matrices to removably attach the prosthesis to the ball attachments of the dental implants. A dental implant, which is a surgical component that interfaces with the bone of the jaw or skull of a dental patient to support the dental prosthesis, must first be surgically placed within the dental patient's mouth in order to thereafter attach the dental prosthesis to the dental implant(s).

Preparation of a dental prosthesis, such as a non-splinted overdenture, is preceded by making a physical or digital impression of the dental patient's oral cavity in the area of the restoration site, including the dental implants already inserted within the restoration site. This impression should accurately reflect the physical features of the dental patient's oral cavity, including the dental implants. An accurate impression can yield a well-fitting dental prosthesis that is secure in the patient's mouth, and that is long-lasting and aesthetically pleasing. An ill-fitting dental prosthesis, on the other hand, can increase the patient's risk of infection or disease, and cause shifting in the prepared prosthesis.

Obtaining an accurate impression, and thereafter preparing a well-fitting dental prosthesis, such as a non-splinted overdenture, is not an insignificant task. For example, during fabrication of a dental prosthesis, such as a non-splinted overdenture, errors may occur when transferring a dental implant position(s) from an impression of a patient's oral cavity to the final prosthesis base. However, precision in transferring the implant position(s) to the final prosthesis base is necessary to accurately attach the prosthesis to the dental implant(s) already inserted into the patient's mouth. Currently, conventional casting of a prosthesis base is one of the only manufacturing methods capable of the precision necessary in transferring dental implant positions to the prosthesis base. Conventional casting, however, while requiring extensive, complicated work to prepare the final prosthesis base, further requires additional finishing steps by a dental technician to trim any projections, and can result in bubbles within the casting that reduce the aesthetics and the stability of the final dental prosthesis.

SUMMARY

In one aspect, the problems associated with preparing a well-fitting dental prosthesis with accurately transferred dental implant positions can be addressed by creating a custom dental prosthesis using a computer-aided design/computer-assisted manufacturing (CAD/CAM) system, the dental prosthesis corresponding to a ball attachment(s) on a dental implant(s). For improved positioning of the prosthesis relative to the ball attachment, a gingiva part of the prosthesis includes retention pockets that are enlarged relative to a matrix that mates to the ball attachment, as well as injection channels that extend from the retention pocket to an exterior of the gingiva part. After mating of the matrix to the ball attachment, the positioning of the matrix in the retention pocket is fixed by injection of a curable adhesive into the retention pocket through the injection channels.

The dental prosthesis created via a CAD/CAM system can be fabricated into a final prosthesis base by, for example, milling a final strength, gingiva colored material using the CAD/CAM system, thus, potentially removing the need for casting of the final prosthesis base and the problems associated with such casting.

In one aspect, the CAD/CAM system automatically locates the position(s) of the dental implant(s) on an impression of a patient's oral cavity, and the position(s) is transferred to the final prosthesis base. In another aspect, at least one retention pocket and at least one injection channel are created within the final prosthesis base to compensate for any errors in transferring the position of the dental implant(s) to the final prosthesis base. The retention pocket is of a size that is slightly larger than a matrix that attaches to a ball attachment of a dental implant, while the injection channel extends from the retention pocket to an exterior of the final prosthesis base. In yet another aspect, the final dental prosthesis is completed by filling any retention pockets via the injection channels with an adhesive to secure the matrix (or matrices) to the final prosthesis base.

One embodiment described herein relates to a dental prosthesis. The dental prosthesis includes a fabricated gingiva part that is fabricated out of a final strength, gingiva colored material, at least one retention pocket, and at least one injection channel that extends from the retention pocket to an exterior of the gingiva part. In one aspect, the dental prosthesis further includes at least one manufactured tooth. In another aspect, the retention pocket is formed to be larger than a matrix that corresponds to a ball attachment of a dental implant, and the retention pocket includes the matrix that is attached to the retention pocket via a curable adhesive injected through the injection channel.

Another embodiment described herein relates to a preparation of a dental prosthesis. A gingiva part of the dental prosthesis is digitally designed to include at least one retention pocket and at least one injection channel that extends from the retention pocket to an exterior of the gingiva part. The gingiva part of the dental prosthesis is fabricated out of a final strength, gingiva colored material to create a fabricated gingiva part, the fabricated gingiva part including the retention pocket and the injection channel. In one aspect, the gingiva part is digitally designed using a computer-aided design (CAD) system, and the gingiva part of the dental prosthesis is fabricated using a computer-assisted manufacturing (CAM) milling system. In another aspect, the gingiva part is digitally designed by locating a position of at least one of the retention pocket and the injection channel on the gingiva part. In yet another aspect, the retention pocket is formed to be larger than a matrix that corresponds to a ball attachment of a dental implant. The matrix is placed into the retention pocket, with the matrix having a loose fit with respect to the retention pocket. In another aspect, the gingiva part is placed over the ball attachment of the dental implant with the matrix being mated to the ball attachment, a curable adhesive is injected into the retention pocket by injecting the curable adhesive through the injection channel, and the adhesive is cured to attach the matrix to the retention pocket and to complete the final dental prosthesis.

Another embodiment described herein relates to a computer for producing a dental prosthesis. The computer comprises at least one processor operable to digitally design a gingiva part of the dental prosthesis. The gingiva part is designed to include at least one retention pocket and at least one injection channel that extends from the retention pocket to an exterior of the gingiva part. The positioning of the retention pocket and the injection channel is automatically generated by the at least one processor. In one aspect, the processor is included in a dental computer-aided design/computer-assisted manufacturing (CAD/CAM) device. In another aspect, a milling system is provided that is configured to fabricate the gingiva part out of a final strength, gingiva colored material based on the digital design, the gingiva part including the retention pocket and injection channel. In yet another aspect, the processor is further configured to automatically propose locations of the retention pocket and the injection channel based on stored information, the stored information including at least one of (i) measurements that are above given thresholds related to a minimal thickness of the gingiva part, (ii) measurements that are below given thresholds related to the minimal thickness of the gingiva part, (iii) measurements related to the positioning of the channel, and (iv) measurements related to the angulation of the channel. In another aspect, the processor is further configured to issue a warning if the minimal thickness of the gingiva part is critical for the proposed location of at least one of the retention pocket and the injection channel. In another aspect, the processor is further configured to adjust the proposed location of at least one of the retention pocket and the injection channel based on the stored information.

Another embodiment described herein relates to a sequence of instructions which, when executed by a computer system, cause the computer system to digitally design a gingiva part of a dental prosthesis. The gingiva part is designed to include at least one retention pocket and at least one injection channel that extends from the retention pocket to an exterior of the gingiva part. The positioning of the retention pocket and the injection channel is automatically generated by the computer system. In one aspect, the instructions further cause the computer system to fabricate the gingiva part of the dental prosthesis based on the digital design, the gingiva part including the retention pocket and the injection channel. In another aspect, the instructions further cause the computer system to automatically propose locations of the retention pocket and the injection channel based on stored information, the stored information including at least one of (i) measurements that are above given thresholds related to a minimal thickness of the gingiva part, (ii) measurements that are below given thresholds related to the minimal thickness of the gingiva part, (iii) measurements related to the positioning of the channel, and (iv) measurements related to the angulation of the channel. In yet another aspect, the instructions further cause the computer system to issue a warning if the minimal thickness of the gingiva part is critical for the proposed location of at least one of the retention pocket and the injection channel. In another aspect, the instructions further cause the computer system to adjust the proposed location of at least one of the retention pocket and the injection channel based on the stored information.

The various embodiments described herein can be useful for compensating for errors in the transmission of implant positions on a dental prosthesis, which thereby improves the aesthetics, stability, and ease of production of the final dental prosthesis. The various embodiments described herein can also be useful for producing a final prosthesis base without casting the base in a conventional manner, which thereby reduces the complicated steps of preparing and finishing the prosthesis base, and further removes the issue of bubbles in the cast base that reduce the aesthetics and the stability of the final dental prosthesis.

Further features and advantages, as well as the structure and operation of various embodiments herein, are described in detail below with reference to the accompanying drawings.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1A is a flow diagram of an example procedure for creating a dental prosthesis, in accordance with an example embodiment herein.

Figure 1B:
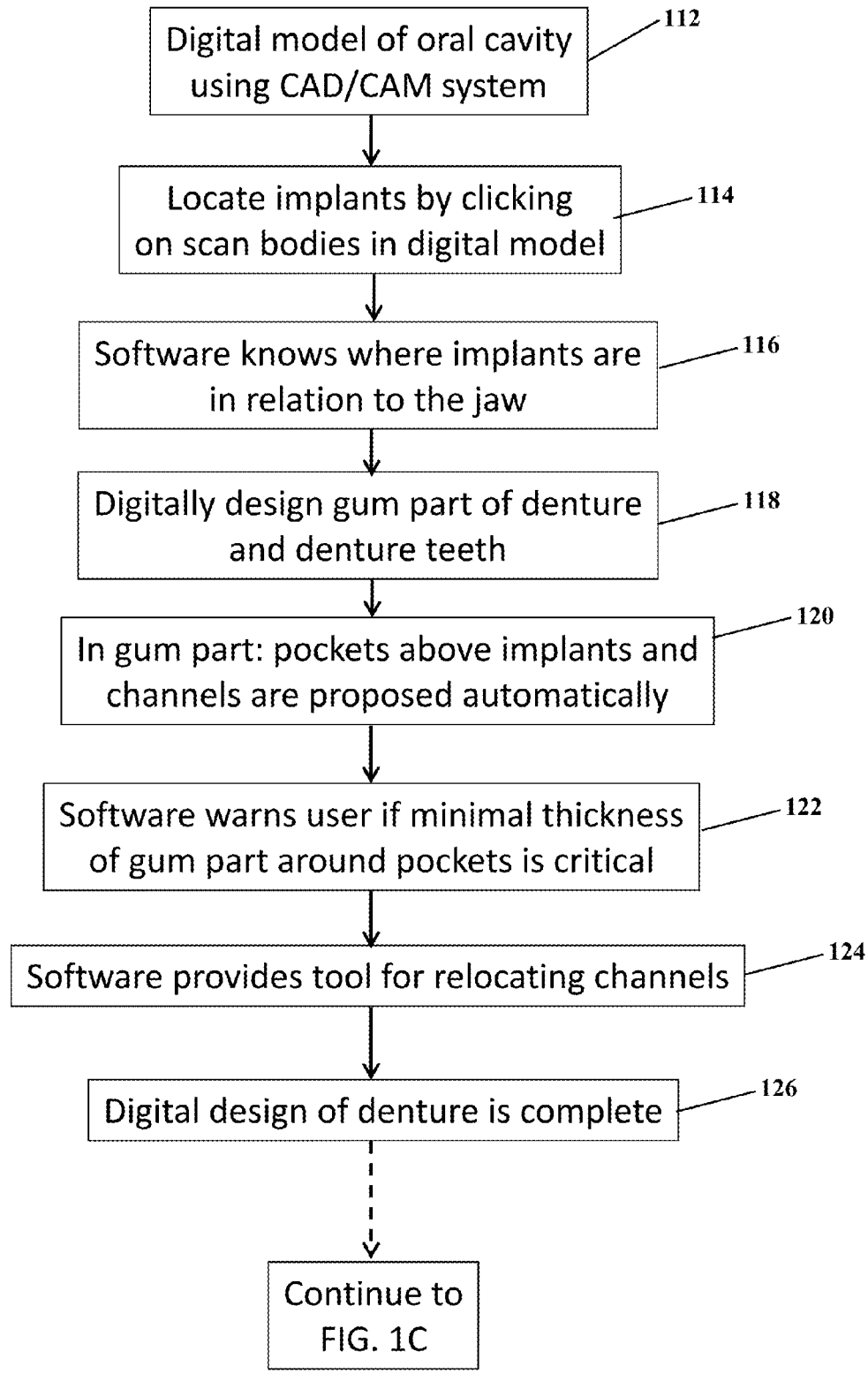
FIG. 1B is a flow diagram of an example procedure for creating a dental prosthesis, in accordance with FIG. 1A.

Different ones of the Figures may have at least some reference numerals that are the same in order to identify the same components, although a detailed description of each such component may not be provided below with respect to each Figure.

DETAILED DESCRIPTION

In accordance with example aspects described herein, methods, systems, apparatuses, and computer programs are provided for creating a dental prosthesis using a CAD/CAM system.

A restoration site is generally an area of a patient's oral cavity in which one or more teeth can be restored, repaired, or replaced by a dental prosthesis. A restoration site may (or may not) include areas in which a tooth or teeth are missing, such as when a patient has lost a tooth or a tooth has been removed during preparation for a dental impression. The restoration site can include teeth adjacent to those that will be directly affected by a dental prosthesis, although it need not include such teeth. A restoration site can include teeth (hard tissue) local to the site, as well as gingiva (soft tissue), and any other portion of the oral cavity local to the site, such as the alveolar bone. The restoration site may (or may not) further include one or more dental implants that interface with the bone of the jaw or skull of a dental patient to support a dental prosthesis. The one or more dental implants must first be surgically placed within the dental patient's mouth in order to thereafter attach the dental prosthesis to the dental implant.

Dental prosthesis generally are, for example, artificial or man-made structures that replace part or all of a patient's dentition at a restoration site. Some examples of dental prosthesis include, without limitation, dental restorations—such as full and partial crowns, bridges, inlays, onlays, and veneers—dentures, and dental implants. A dental prosthesis can be permanent or temporary, and its use may be clinically indicated or elected by a patient.

Figure 1C:
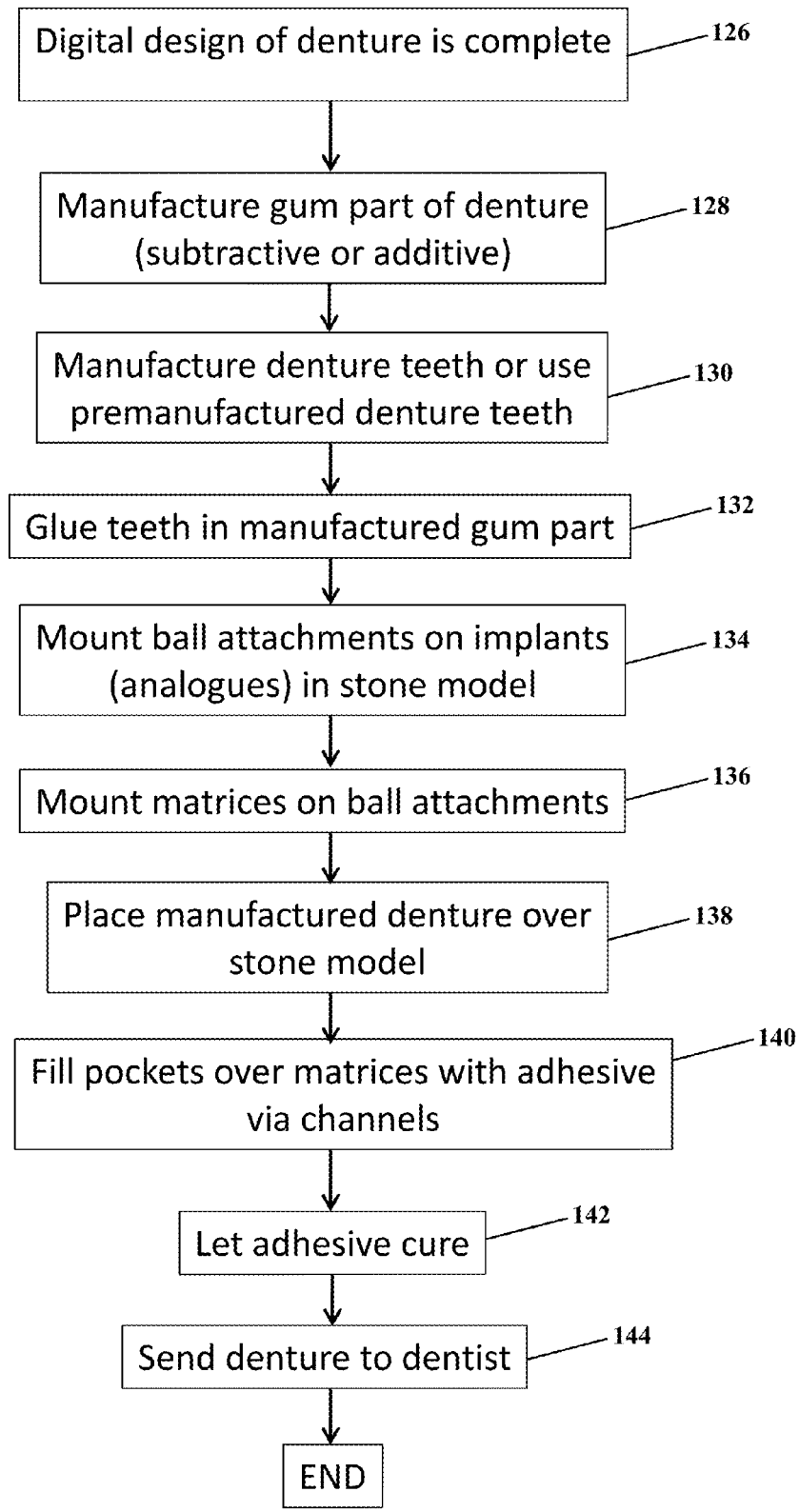
FIG. 1C is a flow diagram of an example procedure for creating a dental prosthesis, in accordance with FIGS. 1A and 1B.

FIGS. 1A-1C illustrate a flow diagram of an example procedure for creating a dental prosthesis configured in accordance with an example embodiment herein. Briefly, according to FIGS. 1A-1C, a dental prosthesis is prepared in which a gingiva part of the dental prosthesis is digitally designed to include at least one retention pocket and at least one injection channel that extends from the retention pocket to an exterior of the gingiva part. The gingiva part of the dental prosthesis is fabricated out of a final strength, gingiva colored material to create a fabricated gingiva part, the fabricated gingiva part including the retention pocket and the injection channel. The gingiva part is digitally designed using a computer-aided design (CAD) system, and the gingiva part of the dental prosthesis is fabricated using a computer-assisted manufacturing (CAM) milling system. In one aspect, the gingiva part is digitally designed by locating a position of at least one of the retention pocket and the injection channel on the gingiva part. In another aspect, the retention pocket is formed to be larger than a matrix that corresponds to a ball attachment of a dental implant. The matrix is placed into the retention pocket, with the matrix having a loose fit with respect to the retention pocket. In yet another aspect, the gingiva part is placed over the ball attachment of the dental implant with the matrix being mated to the ball attachment, a curable adhesive is injected into the retention pocket by injecting the curable adhesive through the injection channel, and the adhesive is cured to attach the matrix to the retention pocket and to complete the final dental prosthesis In more detail, as shown in FIG. 1A, the example procedure begins at step 100 in which a dental patient visits the dentist. In one example embodiment, step 100 occurs after one or more dental implants have been surgically placed within the patient's mouth. Thereafter, at step 102, the dentist will take an impression of the patient's oral cavity. In one example embodiment, the impression is a physical impression. This provides an imprint of the restoration site, which often is made using an intraoral mold, and from which the dental prosthesis, e.g., denture, is produced. In the case of the dentist preparing a physical impression of the patient's oral cavity, the physical impression is thereafter sent to a lab at step 104, where a technician will create a stone model using the physical impression at step 108. The stone model created at step 108 will include analogues of any dental implants that have been implanted within the patient's oral cavity. In one example embodiment, scan bodies are mounted to the dental implant analogues on the stone model in order to allow for scanning and imaging of the stone model and the dental implant analogues. Thereafter, at step 110, the stone model, including the mounted scan bodies, will be scanned using an imaging system, such as, for example, an optical digital camera or any other type of image acquisition device that is capable of generating a three-dimensional model of a real geometry. The scanning of the stone model at step 110 will create a scanned image of the stone model, which is used to produce a digital model of the oral cavity at step 112 using a CAD/CAM system.

Alternatively, in another example embodiment, the impression of the patient's oral cavity taken at step 102 is a digital impression that is produced using an imaging system, such as, for example, an optical digital camera or another type of image acquisition device, as discussed above. In various examples, an optical digital camera can perform imaging procedures and generate image data intra-orally (e.g., image acquisition occurring inside of a patient's mouth) and/or extraorally (e.g., image acquisition occurring outside of a patient's mouth). Also in various examples, an optical digital camera can perform image acquisition either automatically, e.g., without user intervention, or manually in response to operator commands. In one embodiment, the digital impression is created by conducting an intra-oral scan of the patient's oral cavity in which scan bodies are mounted on any dental implants that have been implanted within the patient's oral cavity. The intra-oral scan can be conducted by placing an optical digital camera inside the patient's mouth, and capturing images of the patient's specific oral cavity, including the mounted scan bodies. Using various patterns of color and/or light, it is possible to scan height variations of the features and/or dental implants within the oral cavity and to generate three-dimensional data from the scans. Alternatively, a laser-based scanner could be used to measure distances and/or heights of features and/or dental implants within the patient's oral cavity over a specific area.

Once the digital impression is captured of the patient's oral cavity, such as, for example, via the intra-oral scan, the digital impression of the patient's oral cavity (as opposed to the physical impression discussed above) will be sent to a lab in step 106. This digital impression of the patient's oral cavity, which includes the scan bodies, is thereafter used to create a digital model of the patient's oral cavity using a CAD/CAM system at step 112. The digital model created at step 112 using the CAD/CAM system will be substantially similar, if not identical, to that prepared above in which a physical impression is first taken of the patient's oral cavity.

The digital model of the oral cavity is thus created either from a physical impression (steps 104, 108, and 110) or from a digital impression (step 106). Once the digital model of the patient's oral cavity is created in step 112 using a CAD/CAM system, a digital model of the dental prosthesis is created, as described below, beginning at step 114. A technician locates any dental implants in the digital model at step 114 by first locating any scan bodies included within the digital model. In one embodiment, the CAD/CAM system includes software that allows for locating of the dental implants in the digital model at step 114 by clicking on the scan bodies included within the digital model using, for example, a button on an input unit, such as a mouse. In one example embodiment, at step 116, the software included with the CAD/CAM system understands where the scan bodies, and thus, the dental implants, are located in relation to the patient's jaw. Using this information related to the dental implants and the patient's jaw, both the gingiva part and at least one tooth of a dental prosthesis, e.g., a denture, is digitally designed using the CAD/CAM system at step 118. The gum or gingiva part of the dental prosthesis will further be designed to include retention pockets and injection channels that extend from the retention pockets to an exterior of the gingiva part. In one example embodiment, the software of the CAD/CAM system will automatically propose locations and/or positions for the retention pockets and the injection channels, which will be fully described hereinafter with respect to FIGS. 2A-2C, 3 and 4A-4D, above the dental implants in the digital design of the dental prosthesis at step 120. The software proposes locations and/or positions that are not only above the dental implants, but that will not intersect with the teeth of the dental prosthesis. In step 122, the software issues a warning to the user or technician if the minimal thickness of the gingiva part of the digital design is critical to the locations proposed for the retention pockets and/or injection channels at step 120. The software, however, further provides a tool at step 124 for relocating the proposed locations of at least the injection channels, which will be more fully described with respect to FIGS. 2A-2C. As discussed in more detail below, these retention pockets and injection channels will correspond to matrices and ball attachments that engage with the dental implants in the patient's oral cavity. In particular, the retention pockets can each be formed to be larger than a matrix that corresponds to a ball attachment of a dental implant, such that the matrix will have a loose fit when placed into the respective retention pocket.

Figure 2A:
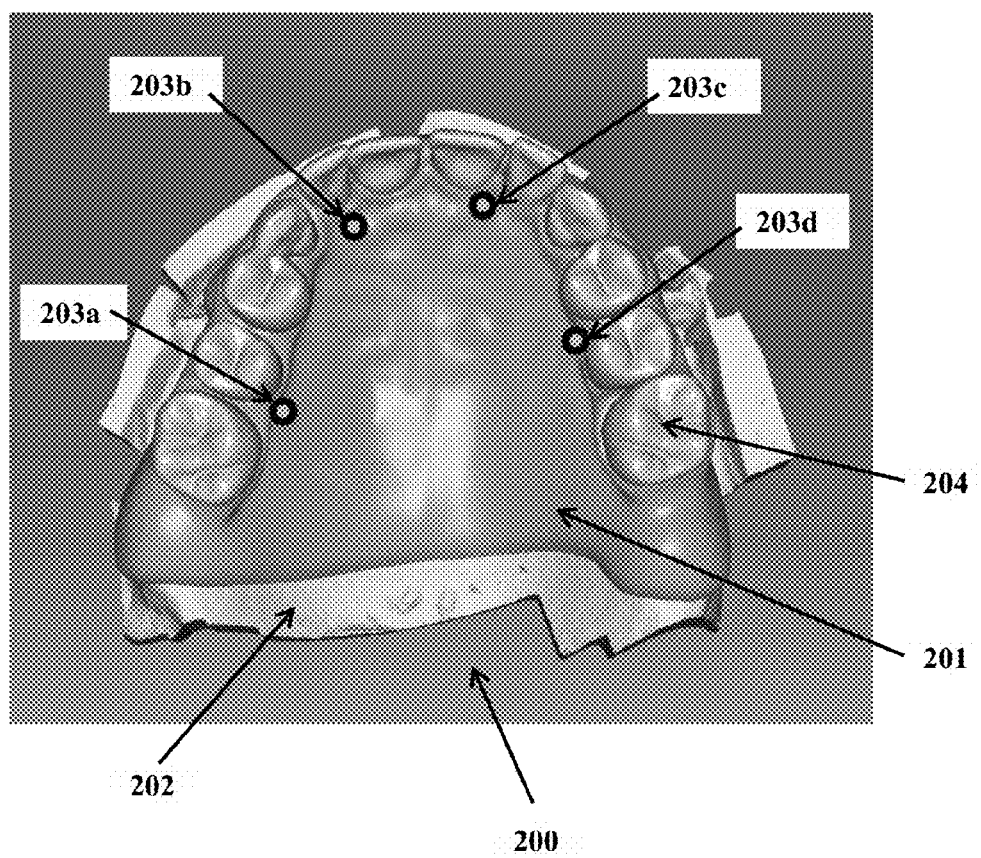
FIG. 2A is a view for illustrating an image of the dental prosthesis configured in accordance with an example embodiment herein.
Figure 2B:
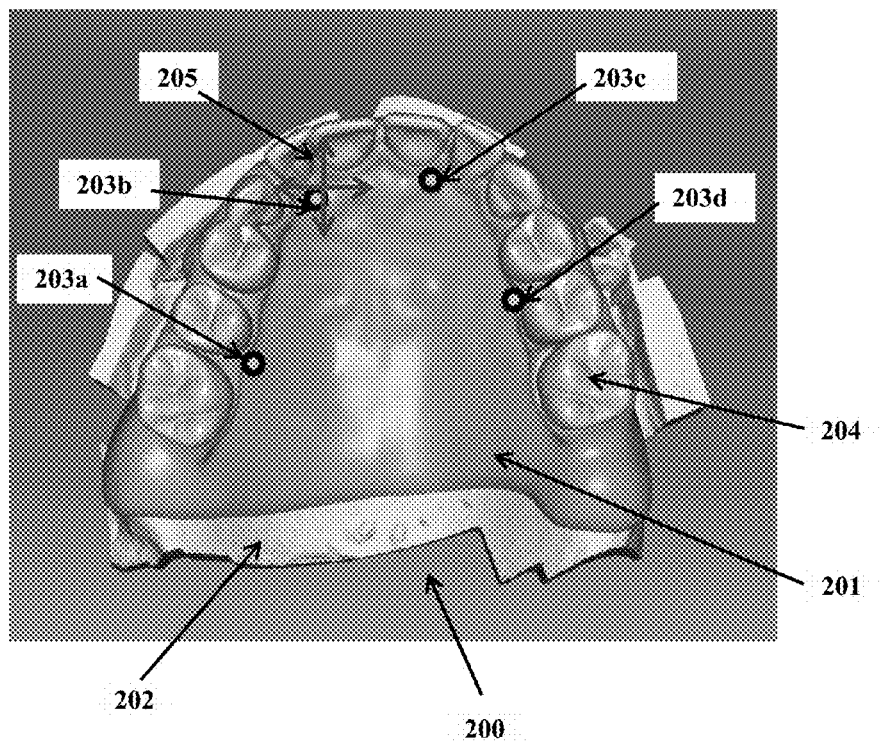
FIGS. 2B and 2C are views for illustrating relocation of channels of a dental prosthesis configured in accordance with an example embodiment herein.
Figure 2C:
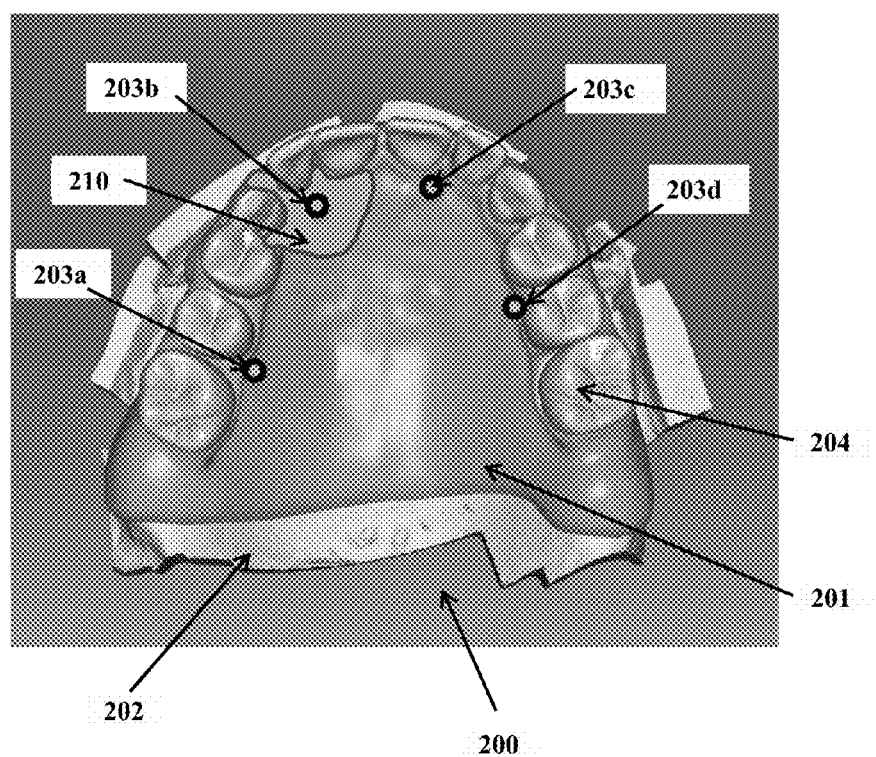

Briefly, according to FIGS. 2A-2C, a computer comprising at least one processor operable to digitally design a gingiva part of a dental prosthesis is provided. The gingiva part is designed to include at least one retention pocket and at least one injection channel that extends from the retention pocket to an exterior of the gingiva part. The positioning of the retention pocket and the injection channel is automatically generated by the at least one processor. In one aspect, the processor is included in a dental computer-aided design/computer-assisted manufacturing (CAD/CAM) device. In another aspect, a milling system is provided that is configured to fabricate the gingiva part out of a final strength, gingiva colored material based on the digital design, the gingiva part including the retention pocket and injection channel. In yet another aspect, the processor is further configured to automatically propose locations of the retention pocket and the injection channel based on stored information, the stored information including at least one of (i) measurements that are above given thresholds related to a minimal thickness of the gingiva part, (ii) measurements that are below given thresholds related to the minimal thickness of the gingiva part, (iii) measurements related to the positioning of the channel, and (iv) measurements related to the angulation of the channel. In another aspect, the processor is further configured to issue a warning if the minimal thickness of the gingiva part is critical for the proposed location of at least one of the retention pocket and the injection channel. In another aspect, the processor is further configured to adjust the proposed location of at least one of the retention pocket and the injection channel based on the stored information.

In more detail, in one example embodiment, as shown in FIG. 2A, a digital design of a dental prosthesis, i.e., a denture 200, is created in, for example, steps 118 and 120, as discussed above. In the digital design of the denture 200, a digital image of the stone model 202 is illustrated, as well as the digitally designed gum or gingiva part 201 and denture teeth 204. As discussed above with respect to step 120 of FIG. 1B, the digital design of the denture 200 further includes proposed locations for retention pockets and/or injection channels 203a-203d that can be automatically proposed by software included with the CAD/CAM system.

In another example embodiment, as shown in FIG. 2B, the software includes a tool 205 that allows for relocating the proposed locations and/or positions for the retention pockets and/or the injection channels 203a-203d in the digital design of the denture 200, as discussed above with respect to step 124 of FIG. 1B. This tool 205 can be used to move and/or rotate the proposed location and/or position of the retention pockets and/or injection channels 203a-203d by clicking the tool 205 on the proposed channel location 203a-203d with a button of an input unit, such as a mouse, and by moving or rotating the tool 205 and thus, the channel 203a-203d, to another location or position by, for example, holding down the button of the input unit until the alternate location or position is selected. In the embodiment of FIG. 2C, the software further provides a highlighted area 210 around the proposed location for the retention pockets and/or injection channels 203a-203d in which the user or technician can effectively move the proposed location 203a-203d. In one example embodiment, the highlighted area 210 is preferably of a color that is distinctive from the gingiva part 201 and/or the injection channels 203a-203d, such as, for example, an orange color. The highlighted area 210 is created from various information collected by the system. In one example embodiment, this information includes: (i) measurements that are above and/or below given thresholds related to the minimal thickness of the gum or gingiva part that is critical for accurate placement of the retention pockets and/or channels on the gingiva part 201, such as that discussed above with respect to step 122 of FIG. 1B, (ii) measurements related to the positioning of the channels, such that the channels will not intersect with the teeth of the dental prosthesis, and/or (iii) measurements related to the angulation of the channels. With respect to the angulation of the channels, in one example embodiment, the angulation is related to an occlusal plane below a given threshold. This threshold may be dependent upon the method and/or machine for manufacturing the dental prosthesis, such that, for example, with an additive method of manufacture, no threshold is possible, but with a subtractive method of manufacture, a threshold of up to 30 degrees may be possible, depending on the machine type. For example, when manufacturing a dental prosthesis with the injection channels via a subtractive method of manufacture, a machine can be used to mill or grind the dental prosthesis out of a prosthesis base material, but such a machine can only be used up to a certain angle related to the main production direction, e.g., the machine limit. Thus, the machine is not capable of rotating the prosthesis base material to any angle before grinding or milling the base material into the dental prosthesis and/or the base material itself may block access to certain parts. In view of the foregoing, the angle of the injection channels may be limited by the method and/or machine for manufacturing the dental prosthesis. In the embodiments of FIGS. 2B and 2C, both the highlighted area 210, as well as the tool 205, can include information related to the positioning and/or angulation of the injection channels 203a-203d to ensure accurate placement on the gingiva part 201 of the digitally designed dental prosthesis.

Once the CAD/CAM system and/or the user is finished with the digital design of the gingiva part 201, the teeth 204, and the locations of the retention pockets and/or injection channels 203a-203d, the digital design of the denture 200 is complete at step 126 of FIG. 1B. In one example embodiment, once the digital design of the denture 200 is complete at step 126, the gingiva part of the denture is fabricated at step 128 using either an additive or subtractive manufacturing procedure. One example embodiment of an additive procedure for fabricating the gingiva part of the denture is stereolithography or optical fabrication. Another example embodiment of an additive manufacturing procedure is 3D-printing of plastics and/or wax. However, a person skilled in the relevant art(s) could fabricate the invention using other additive manufacturing procedures, and doing so is within the scope of the invention.

In one example embodiment of a subtractive manufacturing procedure, the CAD/CAM system works with a milling system or milling machine to fabricate the gingiva part of the denture. The gingiva part can be fabricated by the milling system out of a final-strength prosthesis base material that is preferably made of a gingiva colored material. In an example embodiment, a milling system includes a milling machine having one or more computer-controlled burrs or other grinding and/or cutting components to mill, cut and/or grind a final-strength prosthesis base material block into the pre-determined shape of the gingiva part of the denture based on the CAD/CAM digital model created in step 126 of FIGS. 1B and 1C, thereby producing a final dental prosthesis base.

The final dental prosthesis base, fabricated by either an additive or subtractive manufacturing procedure, will include the retention pockets and injection channels, discussed above. The retention pockets each comprise a spacer of a size that corresponds to matrices and ball attachments that engage with dental implants in the patient's oral cavity (see, e.g., FIGS. 3 and 4A-4D). The injection channels, which are connected to the retention pockets, are preferably provided on the lingual side of the patient's oral cavity (see, e.g., FIG. 3). The injection channels are included to provide access to the retention pockets, such that a curable adhesive can be applied to the area around the corresponding retention pocket and its associated matrix (see, e.g., FIG. 4C). As discussed above, producing a final prosthesis base from a final strength, gingiva colored material using a CAD/CAM system allows for efficiently locating the position(s) of the dental implant(s) on a physical or digital impression of a patient's oral cavity, and accurately transferring the position(s) to the final prosthesis base, such that the final dental prosthesis will easily and securely attach to the dental implants of the patient's oral cavity. By including the retention pockets with the final prosthesis base, any minor errors or imprecisions in the transferring of the positions of the patient's dental implants to the final prosthesis base can be compensated for, as discussed in more detail below. Moreover, by producing a final prosthesis base without casting the base in a conventional manner, the complicated steps of preparing and finishing the prosthesis base are largely reduced, and the issue of bubbles in the cast base that reduce the aesthetics and the stability of the final dental prosthesis can be removed.

In one example embodiment, once the gingiva part of the denture is manufactured in step 128, the denture teeth of the denture prosthesis need to be produced. As described in step 130 of FIG. 1C, the denture teeth can be manufactured by, for example, milling or grinding the denture teeth from a ceramic or metallic block, or another type of material capable of use as a denture tooth. Alternatively, in step 130 of FIG. 1C, the denture teeth can be pre-manufactured teeth, such as those available from VITA Zahnfabrik, Bad Sackingen, Germany, VITA North America, Yorba Linda, Calif., or Heraeus Kulzer North America, South Bend, Ind. Thereafter, in step 132, the teeth can be attached to the manufactured gingiva base by, for example, gluing of the teeth to the gingiva base.

To complete the dental prosthesis, the retention pockets on the gingiva base are filled-in to ensure accurate positioning of the dental prosthesis to the ball attachments of the dental implants in the patient's oral cavity. In one example embodiment, this process begins at step 134 in which ball attachments are mounted or screwed onto dental implant analogues that are included with a prepared stone model, such as the stone model discussed above. Thereafter, in step 136, matrices 304 are mounted onto the ball attachments 305 (see, e.g., FIGS. 3 and 4A-4D) and the fabricated dental prosthesis or denture is placed over the stone model at step 138. The retention pockets 302 of the fabricated dental prosthesis will line-up with the matrices 304 and ball attachments 305 of the dental implants (see, e.g., FIGS. 3 and 4A-4D). However, the retention pockets 302 will comprise a spacer of a size that is slightly larger than the matrices, such that any minor errors in the transferring of the positions of the patient's dental implants to the final prosthesis base can be compensated for, as discussed above.

Figure 3:
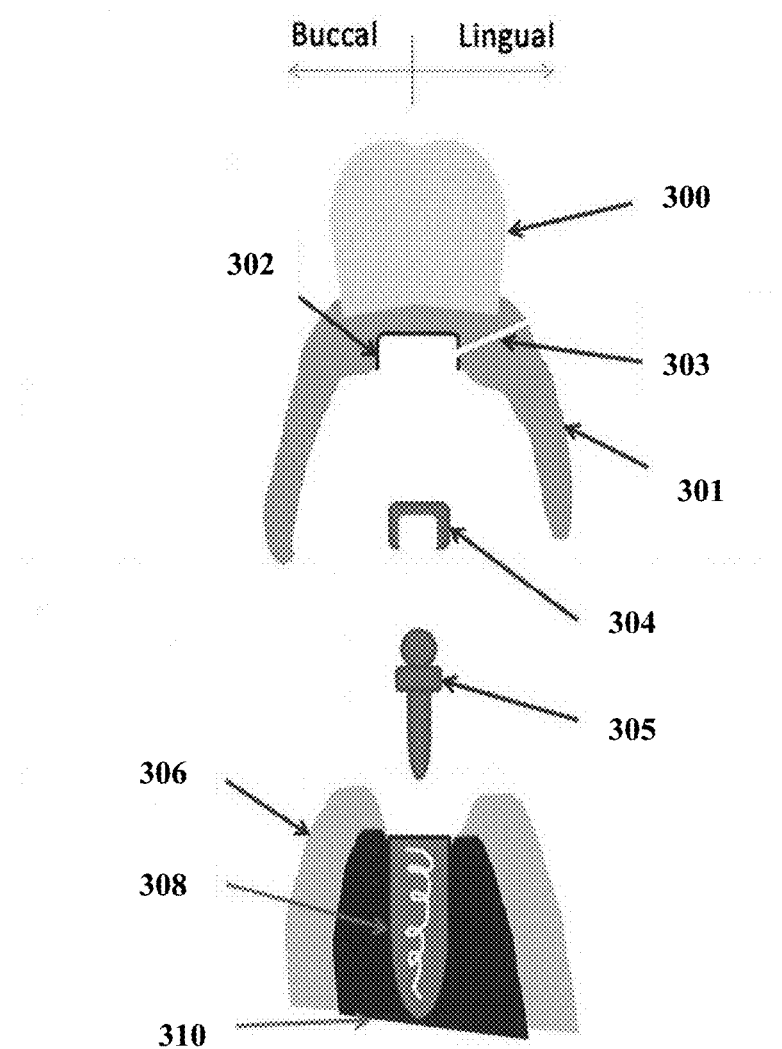
FIG. 3 is a diagram of a dental prosthesis configured in accordance with an example embodiment herein.
Figure 4A:
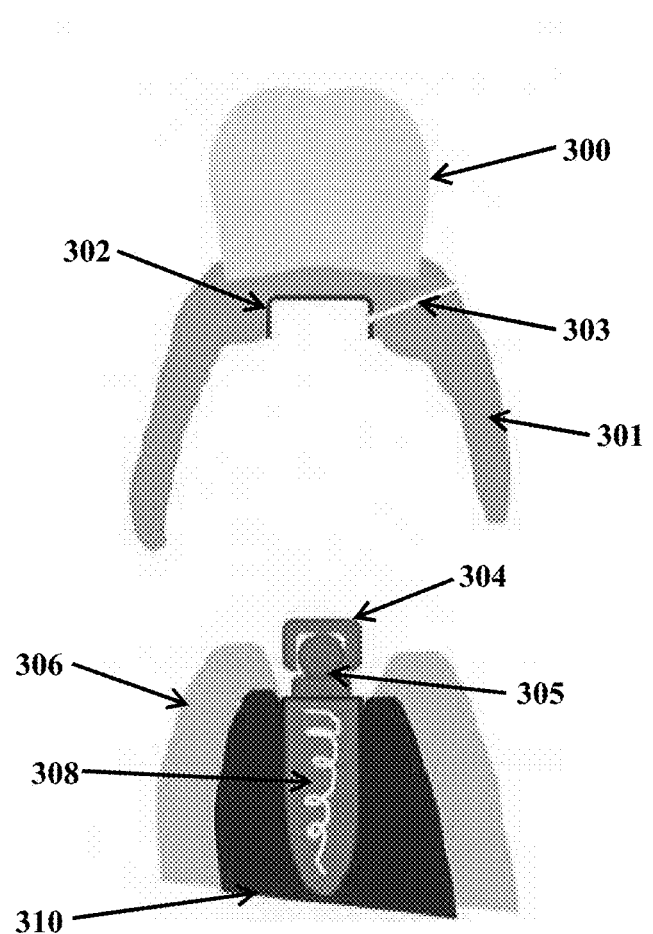
FIG. 4A is a diagram of a first step of an example procedure for completion of a dental prosthesis produced in accordance with an example embodiment herein.
Figure 4B:
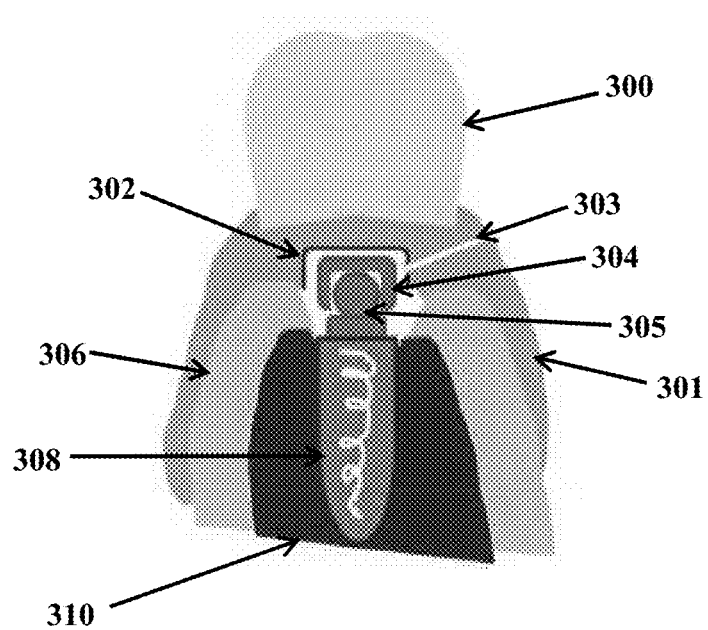
FIG. 4B is a diagram of a second step of an example procedure for completion of a dental prosthesis produced in accordance with an example embodiment herein.
Figure 4C:
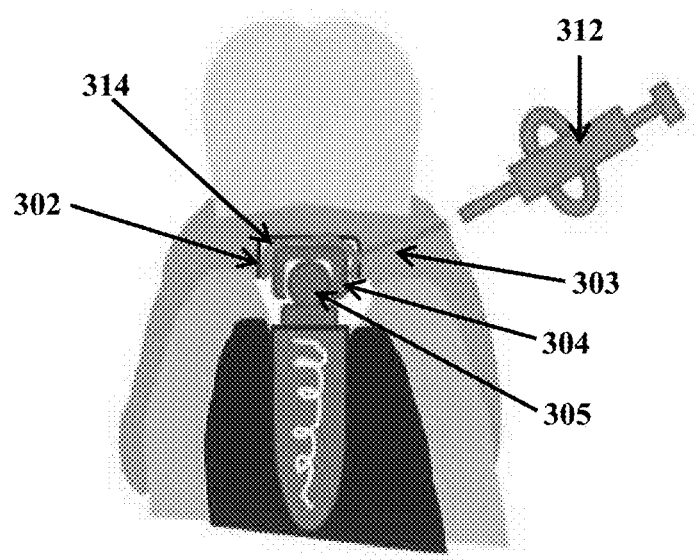
FIG. 4C is a diagram of a third step of an example procedure for completion of a dental prosthesis produced in accordance with an example embodiment herein.
Figure 4D:
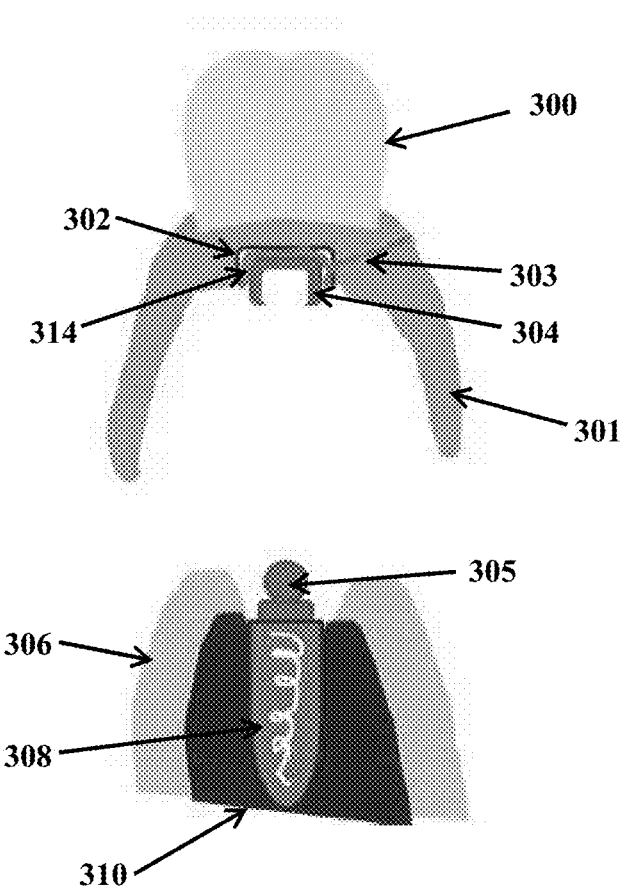
FIG. 4D is a diagram of a fourth step of an example procedure for completion of a dental prosthesis produced in accordance with an example embodiment herein.

This example embodiment is further illustrated in FIGS. 3, 4A and 4B, a final gingiva base 301 comprising at least one attached tooth 300, at least one retention pocket 302, and at least one injection channel 303 is placed onto a matrix 304 and a ball attachment 305 of a dental implant 308 that is included within a stone model representing the gingiva 306 and bone 310 of a patient's oral cavity. However, the retention pocket 302 will be of a size that is slightly larger than the matrix 304 of the ball attachment 305, as shown in, for example, FIG. 4B. Accordingly, in step 140 and/or the embodiment of FIG. 4C, a curable adhesive 314 is used to fill the retention pocket 302 over the matrix 304 using a device, such as a syringe 312, that applies the adhesive to the retention pocket 302 via the injection channel 303. By filling the retention pocket 302 with the adhesive 314, the matrix 304 will become permanently attached to the gingiva base 301 of the dental prosthesis. Moreover, the retention pocket 302 and the injection channel 303 of the dental prosthesis will be filled-in and thus, sealed with the applied adhesive 314. At step 142 of FIG. 1C, the technician lets the adhesive cure or harden to ensure the attachment of the matrix 304 to the gingiva base 301 of the final dental prosthesis. In one example embodiment, any excess adhesive on the dental prosthesis may be removed after curing. In the example embodiment of FIG. 1C and/or FIG. 4D, once the adhesive has cured in step 142, the prosthesis is finished and/or removable. In one example embodiment, the injection channel(s) 303 may also need to be veneered to achieve a perfect aesthetic result. In another example embodiment, any visible transitions between the adhesive-filled injection channel(s) 303 and the gingiva base 301 may be painted to match the gingiva colored material of the fabricated gingiva base 301. Thereafter, in step 144, the final dental prosthesis is removed from the stone model and the final dental prosthesis or denture is sent to the dentist for fitting onto the patient. Although the embodiment described above attaches the matrices 304 to the retention pockets 302 of the final gingiva base 301 by placing the fabricated dental prosthesis over a stone model that includes dental implant analogues, it may be possible to attach the matrices 304 to the final prosthesis base 301 by injecting the curable adhesive into the injection channels 303 while the final prosthesis base sits on the actual dental implants within the patient's mouth.

Figure 5:
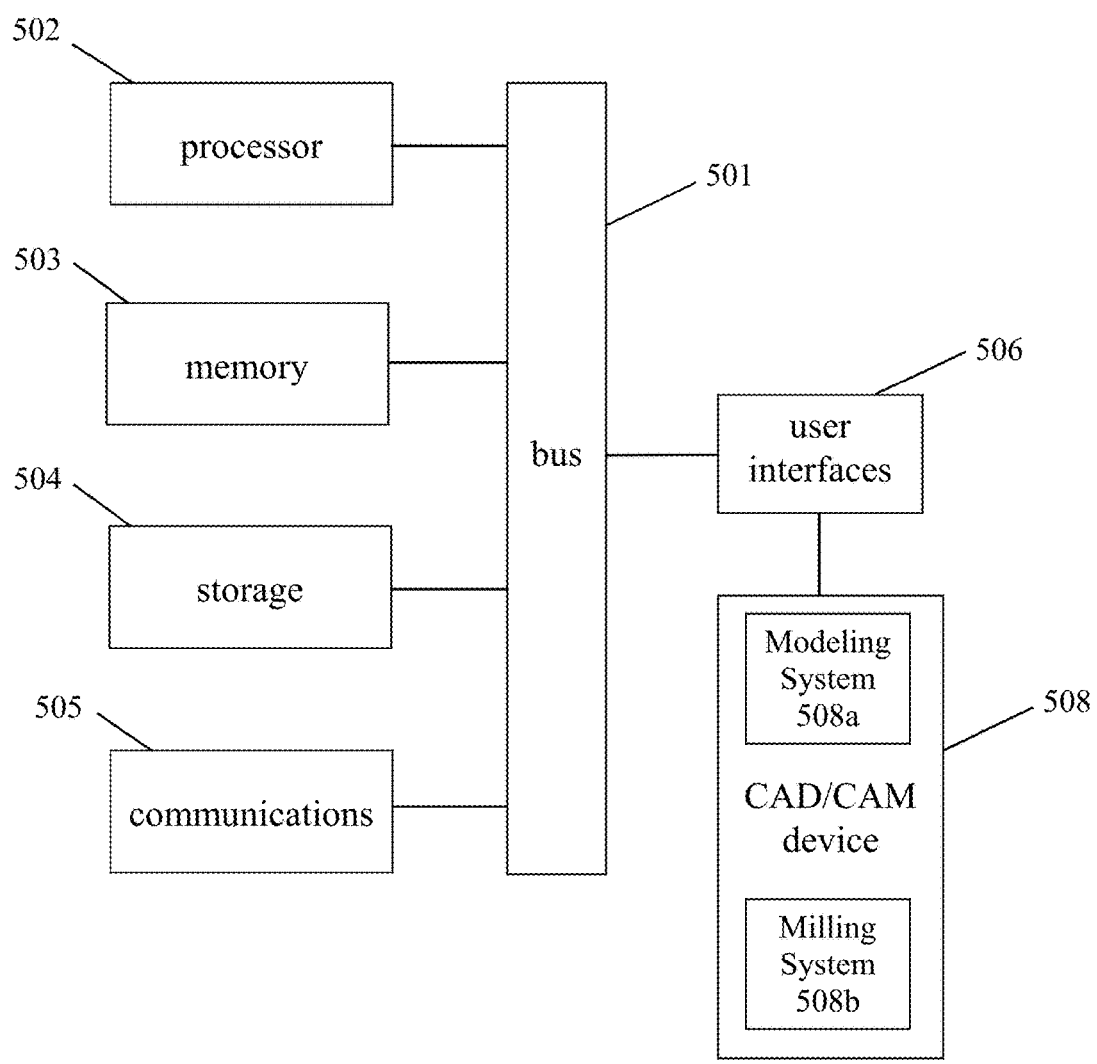
FIG. 5 is an architecture diagram of an example computer system or device which can be used in the practice of example embodiments herein.

FIG. 5 is a diagram of an example computer system. The system, in one example embodiment, may form at least part of the CAD/CAM system used in preparing the dental prosthesis of the present invention, and may be configured to perform one or more steps of the procedure illustrated in FIGS. 1A-1C. The system of FIG. 5 includes a processor 502, a memory 503, a storage device 504, a communications device 505, user interfaces 506, and a CAD/CAM device 508, all of which are coupled to a bus 501.

Processor 502 communicates with the other components of the computer system through bus 501. Storage device 504 includes one or more computer-readable media. Storage device 504 is configured to read and write data including program instructions that may be executed by processor 502 and operating systems (e.g., a general-purpose operating system, such as Microsoft Windows and UNIX, or a custom operating system) that allow processor 502 to control the operation of the other components. Communications device 505 is configured to allow processor 502 to communicate with, for example, a network and the internet. User interfaces 506 can include input devices (e.g., keyboards, mice, joysticks, trackpads, stylus tablets, microphones, and cameras), output devices (e.g., video displays, printers, and speakers), and input/output devices (e.g., touch screens). User interfaces 506 can form at least part of any of the devices, components, and/or systems discussed herein. The CAD/CAM device 508 includes a modeling system 508a configured to perform the digital designing of the gingiva part, with the retention pockets and the injection channels, and the denture teeth, as discussed above. The CAD/CAM device 508 further includes a milling system 508b configured to perform the fabricating of the digitally designed gingiva part that includes the retention pockets and the injection channels, as also discussed above. In one embodiment, the gingiva part is fabricated by the milling system 508b out of a final-strength prosthesis base material that is preferably made of a gingiva colored material. The CAD/CAM device 508 can form at least part of any of the devices, components, and/or systems discussed herein.

Processor 502 is configured to perform part (or all) of any of the procedures described herein. For example, one or more steps of the procedure illustrated in FIGS. 1A-1C can be stored on storage device 504 in the form of computer-readable program instructions. To execute a procedure, the processor loads the appropriate instructions, as stored on storage device 504, into memory 503, and then executes the loaded instructions.

In the foregoing description, example aspects of the invention are described with reference to several example embodiments. Accordingly, the specification should be regarded as illustrative, rather than restrictive. Similarly, the figures illustrated in the drawings, which highlight the functionality and advantages of the invention, are presented for example purposes only. The architecture of the present invention is sufficiently flexible and configurable, such that it may be utilized (and navigated) in ways other than those shown in the accompanying figures.

Software embodiments of example aspects of the invention may be provided as a sequence of instructions, or software, which may be stored on an article of manufacture, e.g., a computer-readable medium having instructions. The instructions on the computer-readable medium may be used to program a computer system or other electronic device. The computer-readable medium may include, but is not limited to, floppy diskettes, optical disks, CD-ROMs, and magneto-optical disks or other types of media suitable for storing electronic instructions.

The techniques described herein, when performed using a computer system, are not limited to any particular software configuration. They may find applicability in any computing or processing environment. The terms "computer-readable medium" and "memory" refer to any medium that is capable of storing, encoding, or transmitting a sequence of instructions for execution by a computer system and that causes the computer system to perform any technique described herein. Furthermore, it is common in the art to speak of software, in one form or another (e.g., program, procedure, process, application, logic, and so on) as taking an action or causing a result. Such expressions are merely a shorthand way of stating that the execution of the software by a computer system causes the processor to perform an action to produce a result. In other embodiments, functions performed by software can instead be performed by hardcoded modules, and thus the invention is not limited only for use with stored software programs. In addition, it is not necessary that procedures described herein be performed with a computer system, and instead they can be performed, in whole or in part, by a human operator.

Although example aspects of the invention have been described in certain specific embodiments, many additional modifications and variations would be apparent to those skilled in the art. It thus should be understood that this invention may be practiced in ways other than those specifically described. Thus, the present example embodiments, again, should be considered in all respects as illustrative and not restrictive.

What is claimed is:

1. A method for preparing a dental prosthesis, the method comprising:
    digitally designing a gingiva part of the dental prosthesis, wherein the gingiva part is designed to include at least one retention pocket and at least one injection channel that extends from the retention pocket to an exterior of the gingiva part; and
    fabricating the gingiva part of the dental prosthesis out of a final strength, gingiva colored material to create a fabricated gingiva part, the fabricated gingiva part including the retention pocket and the injection channel,
    wherein a position of the retention pocket and the injection channel is automatically generated by a processor that performs the digital designing of the gingiva part.

2. The method according to claim 1, wherein the retention pocket is formed to be larger than a matrix that corresponds to a ball attachment of a dental implant.

3. The method according to claim 2, further comprising placing a matrix into the retention pocket, the matrix having a loose fit with respect to the retention pocket.

4. The method according to claim 3, further comprising:
    placing the gingiva part over the ball attachment of the dental implant with the matrix being mated to the ball attachment;
    injecting a curable adhesive into the retention pocket by injecting the curable adhesive through the injection channel; and
    curing the adhesive to attach the matrix to the retention pocket.

5. The method according to claim 4, further comprising painting the cured adhesive to match the gingiva colored material of the fabricated gingiva part.

6. The method according to claim 1, wherein the digitally designing the gingiva part is performed by a computer-aided design (CAD) system, and the fabricating of the gingiva part of the dental prosthesis is performed using a computer-assisted manufacturing (CAM) milling system.

7. A system for producing a dental prosthesis, the system comprising at least one processor operable to digitally design a gingiva part of the dental prosthesis, wherein the gingiva part is designed to include at least one retention pocket and at least one injection channel that extends from the retention pocket to an exterior of the gingiva part, the positioning of the retention pocket and the injection channel being automatically generated by the at least one processor.

8. The system according to claim 7, wherein the at least one processor is included in a dental computer-aided design/computer-assisted manufacturing (CAD/CAM) device.

9. The system according to claim 7, wherein the system further comprises a milling system configured to fabricate the gingiva part out of a final strength, gingiva colored material based on the digital design, the gingiva part including the retention pocket and the injection channel.

10. The system according to claim 7, wherein the processor is further configured to automatically propose locations of the retention pocket and the injection channel based on stored information, the stored information including at least one of (i) measurements that are above given thresholds related to a minimal thickness of the gingiva part, (ii) measurements that are below given thresholds related to the minimal thickness of the gingiva part, (iii) measurements related to the positioning of the channel, and (iv) measurements related to the angulation of the channel.

11. The system according to claim 10, wherein the processor is further configured to issue a warning if the minimal thickness of the gingiva part is critical for the proposed location of at least one of the retention pocket and the injection channel.

12. The system according to claim 10, wherein the processor is further configured to adjust the proposed location of at least one of the retention pocket and the injection channel based on the stored information.

13. A non-transitory computer-readable medium storing sequences of instructions, the sequences of instructions including instructions which, when executed by a computer system, cause the computer system to:
digitally design a gingiva part of a dental prosthesis, wherein the gingiva part is designed to include at least one retention pocket and at least one injection channel that extends from the retention pocket to an exterior of the gingiva part, the positioning of the retention pocket and the injection channel being automatically generated by the computer system.

14. The non-transitory computer-readable medium according to claim 13, wherein the instructions, when executed by the computer system, further cause the computer system to fabricate the gingiva part of the dental prosthesis based on the digital design, the gingiva part including the retention pocket and the injection channel.

15. The non-transitory computer-readable medium according to claim 13, wherein the instructions, when executed by the computer system, further cause the computer system to automatically propose locations of the retention pocket and the injection channel based on stored information, the stored information including at least one of (i) measurements that are above given thresholds related to a minimal thickness of the gingiva part, (ii) measurements that are below given thresholds related to the minimal thickness of the gingiva part, (iii) measurements related to the positioning of the channel, and (iv) measurements related to the angulation of the channel.

16. The non-transitory computer-readable medium according to claim 15, wherein the instructions, when executed by the computer system, further cause the computer system to issue a warning if the minimal thickness of the gingiva part is critical for the proposed location of at least one of the retention pocket and the injection channel.

17. The non-transitory computer-readable medium according to claim 15, wherein the instructions, when executed by the computer system, further cause the computer system to adjust the proposed location of at least one of the retention pocket and the injection channel based on the stored information.

* * * * *